US006657057B2

(12) United States Patent
Hisatake et al.

(10) Patent No.: US 6,657,057 B2
(45) Date of Patent: Dec. 2, 2003

(54) PROCESS FOR PRODUCTION OF METHYLCOBALAMIN

(75) Inventors: Yoshihiko Hisatake, Ibaraki (JP); Hiroshi Kuroda, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 10/130,797

(22) PCT Filed: Dec. 7, 2000

(86) PCT No.: PCT/JP00/08675

§ 371 (c)(1),
(2), (4) Date: May 23, 2002

(87) PCT Pub. No.: WO01/42271

PCT Pub. Date: Jun. 14, 2001

(65) Prior Publication Data

US 2002/0183511 A1 Dec. 5, 2002

(30) Foreign Application Priority Data

Dec. 9, 1999 (JP) .......................................... 11/350683
Jun. 23, 2000 (JP) ...................................... 2000-188619

(51) Int. Cl.$^7$ .............................................. C07H 11/04
(52) U.S. Cl. ..................... 540/452; 536/117; 536/17.1; 536/26.41
(58) Field of Search .......................... 540/452; 536/117, 536/17.1, 26.41

(56) References Cited

U.S. PATENT DOCUMENTS 3,773,756 A   11/1973  Penasse et al. ............. 540/452
3,789,211 A   1/1974   Mervyn et al.
3,928,320 A   12/1975  Boige ......................... 540/452

FOREIGN PATENT DOCUMENTS

| DE | 2019176 | 11/1971 |
| FR | 2240232 | 3/1975 |
| GB | 1306958 | 2/1973 |
| GB | A 1355899 | 6/1974 |
| GB | 1355899 A | 6/1974 |
| JP | 45-38059 | 12/1970 |
| JP | A 45-38059 | 12/1970 |
| JP | A 49-47899 | 5/1974 |
| JP | A 50-14900 | 4/1975 |
| JP | A 50-38120 | 12/1975 |
| JP | 8-143590 | 6/1996 |

OTHER PUBLICATIONS

Rachkus et al., Leituvos Tsr Mokslu Akademijos Darbai, C. Serija, Biologijos Mokslai, Mokslas, Vilnius, Lt., No. 1, pp. 133–141 (1979).

Haglund et al., Chem. Res. Toxicol., Vol. 13, No. 22, pp. 253–256, (2000).

*Primary Examiner*—John M. Ford
(74) *Attorney, Agent, or Firm*—Birch, Stewart, Kolasch & Birch, LLP

(57) ABSTRACT

The present invention provides an industrially excellent and novel process for producing methylcobalamin useful as medicines. Namely, it provides a process for producing methylcobalamin, which comprises the step of methylating cyanocobalamin or hydroxocobalamin in the presence of a reducing agent and a water-soluble methylating agent.

10 Claims, No Drawings

PROCESS FOR PRODUCTION OF METHYLCOBALAMIN

This application is the national phase under 35 U.S.C. §371 of PCT International Application No. PCT/JP00/08675 which has an International filing date of Dec. 7, 2000, which designated the United States of America.

FIELD OF THE INVENTION

Methylcobalamin is a coenzyme-type vitamin $B_{12}$ existing in blood and cerebrospinal fluid and is excellent in migrating ability to nervous tissues as compared with other $B_{12}$ homologs. Biochemically, it exhibits a pharmacological action of accelerating metabolism of nucleic acids, proteins and lipids by methyl group rearrangement and thereby restoring damaged nervous tissues. Based on these properties, it has been clinically employed for preventing, treating or improving peripheral neuropathy such as diabetic neuropathy and polyneuritis, particularly numbness, pain and paralysis, and is also effective in megaloblastic anemia owing to vitamin $B_{12}$ deficiency, and thus, it is an important vitamin.

Accordingly, the present invention relates to an industrially excellent and novel process for producing methylcobalamin useful as medicines.

PRIOR ART

Methylcobalamin has been hitherto produced mainly by the following synthetic methods:

(1) a method of reacting hydroxocobalamin with a dicarboxylic acid monomethyl ester in the presence of a metal powder (JP-A 49-47899);

(2) a method of reacting cyanocobalamin with monomethyl oxalate in the presence of a metal powder in hydrous methanol (JP-A 50-41900);

(3) a method of reacting hydroxocobalamin with methylmercury iodide or ammonium methylhexafluorosilicate (JP-B 50-38120); and (4) a method of reacting cyanocobalamin with methyl iodide in the presence of sodium borohydride (JP-B 45-38059).

However, dicarboxylic acid monomethyl esters such as monomethyl oxalate to be used in the methods (1) and (2) are not commercially available and hence are necessary to prepare in use, so that it is impossible to utilize them industrially. Furthermore, zinc powder to be used as the metal powder is a heavy metal and hence it is inevitable to take measures for preventing its contamination into products and for protecting the environment, so that the powder is industrially not preferable.

Moreover, methylmercury iodide to be used in (3) is a pollutant and hence cannot be employed industrially. Furthermore, ammonium methylhexafluorosilicate is also not commercially available and hence is necessary to prepare in use, so that it is impossible to utilize it industrially.

On the other hand, the synthetic method (4) is a very excellent method in view of yield and product purity, but is not satisfactory as an industrial process because methyl iodide has an extremely low boiling point (41 to 43° C.) and is difficult to handle. Furthermore, from the viewpoint of protecting working environment or natural environment, the use of methyl iodide assigned as a specified chemical substance and having toxicity such as possibility of carcinogenicity is by no means preferable in view of industrial health of factory workers. Moreover, in order to obtain highly pure methylcobalamin by the method of using methyl iodide, operation for purification by one or more kinds of column chromatography is usually necessary, which is a serious problem from operational viewpoint and viewpoint of production cost. In addition, the quantity of organic solvents for use in the column purification is large and also waste liquid quantity tends to be enormous.

Thus, an industrially excellent process for producing methylcobalamin is not completely established yet and hence a novel excellent method has been desired.

DISCLOSURE OF THE INVENTION

The present inventors have extensively studied for the purpose of improving the above problems. As a result, surprisingly, they have found that aimed methylcobalamin can be conveniently, safely, and inexpensively obtained in high yields by the below-mentioned method, and thus accomplished the present invention.

Accordingly, the present invention provides an industrially excellent process for producing methylcobalamin, particularly a novel process using no methyl iodide and no purification by column chromatography.

The following will explain the present invention in detail.

The present invention relates to a process for producing methylcobalamin (V), which is represented by the following chemical reaction formula:

Cobalamin-CN or Cobalamin-OH→Cobalamin-CH$_3$

Cyanocobalamin (I), hydroxocobalamin (II), and methylcobalamin (V) according to the present invention are known natural compounds and are represented by the following chemical formula:

Cyanocobalamin, CAS Res. No.: 68-19-9
Hydroxocobalamin, CAS Res. No.: 13422-51-0
Methylcobalamin, CAS Res. No.: 13422-55-4

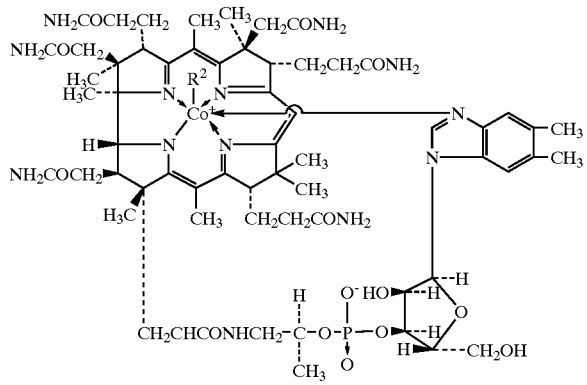

$R^2$=CN: Cyanocobalamin (I)
$R^2$=OH: Hydroxocobalamin (II)
$R^2$=CH$_3$: Methylcobalamin (V)

The characteristic feature of the present invention is that a highly pure methylcobalamin equal to or superior to the product purified by column chromatography can be conveniently obtained in high yields only by methylating cyanocobalamin (I) or hydroxocobalamin (II) in the presence of a reducing agent (III) and a water-soluble methylating agent (IV) usually in an aqueous solution or a hydrous organic solvent, if necessary, precipitating the reaction product which is hardly soluble in water as crystals or precipitates, and then separating and treating it.

The water-soluble methylating agent (IV) in the present invention is not limited as far as it's solubility in water is 2% or more, and specifically includes trimethylsulfur derivatives (VI) represented by the following formula, for example.

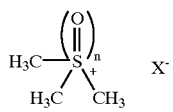

wherein X represents a halogen atom or methoxysulfonyloxy group; and n represents 0 or 1.

Examples of the trimethylsulfur derivatives (VI) include the following compounds but they are not limited thereto.

(1) Trimethylsulfoxonium iodide, CAS Res. No.: 1774-47-6

(2) Trimethylsulfonium iodide, CAS Res. No.: 2181-42-2

(3) Trimethylsulfoxonium chloride, CAS Res. No.: 5034-06-0

(4) Trimethylsulfonium chloride, CAS Res. No.: 3086-29-1

(5) Trimethylsulfoxonium bromide, CAS Res. No.: 3084-53-5

(6) Trimethylsulfoxonium bromide, CAS Res. No.: 25596-24-1

(7) Trimethylsulfonium methyl sulfate, CAS Res. No.: 2181-44-4

All these compounds are known products and, in particular, trimethylsulfoxonium iodide, trimethylsulfonium iodide, trimethylsulfoxonium chloride, trimethylsulfoxonium bromide and trimethylsulfonium bromide are inexpensive and available as industrial starting materials. Moreover, trimethylsulfonium chloride can be easily synthesized and available by the method described in Tetrahedron Lett., 27, 1233 (1986) (B. Byrne et al.).

Among the trimethylsulfur derivatives (VI), trimethylsulfoxonium bromide, trimethylsulfonium bromide, trimethylsulfoxonium chloride and trimethylsulfonium chloride particularly exhibit a high solubility in water and have a characteristic that the use in a smaller amount affords highly pure methylcobalamin in high yields.

The amount of the trimethylsulfur derivative (VI) to be used is not particularly limited, but it is used in an amount of usually 1.0 to 5 equivalents, preferably 1.1 to 4.5 equivalents and more preferably 1.2 to 4 equivalents to cyanocobalamin (I) or hydroxocobalamin (II).

The reducing agent (III) according to the present invention is not particularly limited as far as it is a reducing agent employable in the synthesis of cyanocobalamin (I) or hydroxocobalamin (II). More specifically, examples thereof include sodium borohydride.

The amount of the reducing agent (III) to be used is not particularly limited, but it is used in an amount of usually 5 to 30 equivalents, preferably 8 to 25 equivalents and more preferably 10 to 20 equivalents to cyanocobalamin (I) or hydroxocobalamin (II).

The process according to the present invention enables the production of highly pure methylcobalamin in high yields using no metal ion or using only a small amount thereof as a cyan ion-trapping agent, and the process exhibits an extremely excellent effect in view that no problem arises at removal of metal ion products, which is difficult to filter, from the system.

Generally, when and methyl iodide is used as a methylating agent, ferrous sulfate is used as a cyan ion-trapping agent in combination with those agents in most cases, and it is necessary to use ferrous sulfate in an amount of at least 30% by weight or more relative to cyanocobalamin (I) or hydroxocobalamin (II).

However, in the present invention, it is possible to obtain highly pure methylcobalamin in high yields because methylation proceeds even when no ferrous sulfate is used as a cyan ion-trapping agent.

Furthermore, in the case that ferrous sulfate is used in a small amount as a cyan ion-trapping agent, the reaction proceeds more rapidly and highly pure methylcobalamin can be obtained in high yields by the same post-treatment as in the case that no ferrous sulfate is used. Moreover, in the case that cobalt chloride is used in a small amount, highly pure methylcobalamin can be also obtained in high yields because the methylation proceeds highly selectively and hence the production of impurities is inhibited.

Therefore, the present invention also relates to a process for producing methylcobalamin (V), which comprises the steps of methylating cyanocobalamin (I) or hydroxocobalamin (II) in the presence of a cyan ion-trapping agent, a reducing agent (III) and a water-soluble methylating agent (IV) in an aqueous solution or a hydrous organic solvent; and then precipitating the reaction product as crystals or precipitates.

In the present invention, in the case that a cyan ion-trapping agent is used, examples of the cyan ion-trapping agent include metals or metal salts such as ferrous sulfate, iron powder, Mohr's salt, ferrous chloride, cobalt chloride, nickel chloride and zinc chloride, and particularly preferred are ferrous sulfate and/or cobalt chloride. These metals or metal salts may be used solely or in combination.

The cyan ion-trapping agent may be used in a small amount, and the amount is usually from 1 to 30% by weight and more preferably from 1 to 10% by weight to cyanocobalamin (I) or hydroxocobalamin (II).

Finally, the use of a reaction solvent is not particularly limited, and in the case of using a solvent, it is not particularly limited as far as it is inert to cyanocobalamin (I), hydroxocobalamin (II), trimethylsulfur derivative (VI) or methylcobalamin (V). The reaction solvent is usually an aqueous solution or a hydrous organic solvent. As the organic solvent, preferred is usually a water-soluble one, and examples thereof include lower alcohols such as methanol, ethanol, propanol, isopropanol, butanol, isobutanol, sec-butanol and t-butanol; various esters such as methyl formate, ethyl formate, methyl acetate, ethyl acetate and isopropyl acetate; various ketones such as acetone, 2-butanone and 3-methyl-2-butanone; cyclic ethers such as THF and dioxane; acetonitrile, DMF, DMSO, pyridine etc.; and mixtures containing one or more of them.

The reaction temperature in the present invention is also not particularly limited, but the reaction is conducted at a temperature of usually 0 to 90° C., preferably 10 to 70° C. and more preferably 15 to 50° C.

A more preferred result is obtained by conducting the reaction under a stream of an inert gas such as nitrogen and/or in the dark place (under infrared ray).

In order to explain the present invention specifically, Examples will be described in the following, but the invention is by no means limited thereto.

EXAMPLES

Example 1

Synthesis of Methylcobalamin

The present Example was conducted in the dark place (under infrared ray).

To 260 ml of ion-exchanged water were added 20 g of cyanocobalamin, 6.02 g of trimethylsulfonium iodide and 800 mg of iron(II) sulfate heptahydrate. The mixture was heated in a water bath and, after replacing the atmosphere of the system by nitrogen, a solution of sodium borohydride (8 g)/2N sodium hydroxide (0.2 ml)/water (40 ml) and 15 ml of 2-butanone were added dropwise thereto under stirring at an inner temperature of 40° C. over 20 minutes, respectively. After stirring for 15 minutes as it was, the mixture was cooled to 15° C. Further, 15 ml of 2-butanone was added thereto, followed by stirring overnight. The precipitates were collected by filtration and dried, to give 21.4 g of a crude product of the title compound. Thereto was added 200 ml of a 50% acetone aqueous solution, and the mixture was heated, adjusted to pH 6.5 with concentrated hydrochloric acid and then filtered. After washing with 40 ml of a 50% acetone aqueous solution, 630 ml of acetone was added dropwise to the filtrate, followed by stirring at 15° C. overnight. Precipitated crystals were collected by filtration and dried, to give 17 g of the title compound (yield 86%).

Physical Properties of Mecobalamin Obtained

The hydrochloride buffer (pH 2.0): $UV_{max}$ was detected at 264–266, 303–307 and 459–462 nm.

The phosphate buffer (pH 7.0): $UV_{max}$ was detected at 266–269, 341–344 and 520–524 nm.

Referential values of $UV_{max}$ (Merck Index, 12th edition)

Example 2

Synthesis of Mecobalamin

The present example was conducted in the dark place (under infrared ray).

To 1.3 l of ion-exchanged water were added 100 g of cyanocobalamin and 32.46 g of trimethylsulfoxonium iodide. After replacing the atmosphere of the system by nitrogen, the mixture was heated in a water bath and a solution of sodium borohydride (40 g)/2N sodium hydroxide (2 ml)/water (200 ml) was added dropwise thereto under stirring at an inner temperature of 40° C. over 30 minutes. After stirring for 1 hour as it was, the mixture was cooled to room temperature and then stirred overnight. The precipitates were collected by filtration and dried, to give a crude product of the title compound. Thereto was added 1 l of a 50% acetone aqueous solution, and the mixture was heated, adjusted to pH 6.5 with concentrated hydrochloric acid and then filtered. After washing with 400 ml of a 50% acetone aqueous solution, 2.8 l of acetone was added dropwise thereto and the mixture was stirred at 17° C. overnight. Precipitated crystals were collected by filtration and dried, to give 90 g of the title compound (yield 91%).

Example 3

Synthesis of Mecobalamin

The present Example was conducted in the dark place (under infrared ray).

To 1.3 l of ion-exchanged water were added 100 g of cyanocobalamin and 32.46 g of trimethylsulfoxonium iodide, 4 g of iron(II) sulfate heptahydrate and 100 ml of 2-butanone. Under a nitrogen stream, the mixture was heated in a water bath and a solution of sodium borohydride (40 g)/2N sodium hydroxide (1 ml)/water (200 ml) was added dropwise thereto under stirring at an inner temperature of 40° C. over 30 minutes. After stirring for 30 minutes as it was, the mixture was returned to room temperature and further stirred overnight. The precipitates were collected by filtration and dried, to give 123 g of a crude product of the title compound. Thereto was added 1 l of a 50% acetone aqueous solution, and the mixture was heated at 35° C., adjusted to pH 7.0 with concentrated hydrochloric acid and then filtered. 2.8 l of acetone was added dropwise thereto, followed by stirring overnight. Precipitated crystals were collected by filtration and dried, to give 93.2 g of the title compound (yield 94%).

Example 4

Synthesis of Mecobalamin

The present example was conducted in the dark place (under infrared ray).

To 390 ml of ion-exchanged water were added 30 g of cyanocobalamin, 14.61 g of trimethylsulfoxonium iodide, 900 mg of iron (II) sulfate heptahydrate, 900 mg of cobalt chloride hexahydrate and 22.5 ml of 2-butanone. After replacing the atmosphere of the system by nitrogen, the mixture was heated in a water bath and a solution of sodium borohydride (12 g)/2N sodium hydroxide (1 ml)/water (60 ml) was added dropwise thereto under stirring at an inner temperature of 20° C. After stirring for 3 hours as it was, the mixture was cooled to 10° C. and then stirred overnight. Thereto was added 24 ml of 3-methyl-2-butanone, followed by stirring for 2 hours. Then, the precipitates were collected by filtration and dried, to give 35 g of a crude product of the title compound. Thereto was added 300 ml of a 50% methanol aqueous solution and the mixture was heated at 35° C, filtered and washed with 120 ml of a 50% methanol aqueous solution. After the mixture was adjusted to pH 7.0 with concentrated hydrochloric acid, 1365 ml of acetone was added dropwise thereto and the mixture was stirred at 10° C. overnight. Precipitated crystals were collected by filtration and dried, to give 25.9 g of the title compound (yield 86.3%).

Example 5

Synthesis of Mecobalamin

The present example was conducted in the dark place (under infrared ray).

To 130 ml of ion-exchanged water were added 10 g of cyanocobalamin, 3.83 g of trimethylsulfoxonium bromide, 700 mg of iron (II) sulfate heptahydrate and 7.5 ml of 2-butanone. After replacing the atmosphere of the system by nitrogen, the mixture was heated in a water bath and a solution of sodium borohydride (4 g)/2N sodium hydroxide (0.2 ml)/water (20 ml) was added dropwise thereto under stirring at an inner temperature of 35° C. After stirring for 3 hours as it was, the mixture was cooled to 15° C. and then stirred overnight. Thereto was added 7.5 ml of 2-butanone, followed by stirring for 2 hours. Then, the precipitates were collected by filtration and dried, to give a crude product of the title compound. Thereto was added 140 ml of a 50% acetone aqueous solution, and the mixture was heated at 45° C., filtered and washed with 60 ml of a 50% acetone aqueous solution. After the mixture was adjusted to pH 6.5 with concentrated hydrochloric acid, 475 ml of acetone was added dropwise thereto and the mixture was stirred at 20° C. overnight. Precipitated crystals were collected by filtration and dried, to give 8.86 g of the title compound (yield 89.3%).

Example 6

Synthesis of Mecobalamin

The present example was conducted in the dark place (under infrared ray).

To 650 ml of ion-exchanged water were added 50 g of cyanocobalamin, 19.51 g of trimethylsulfoxonium bromide, 3.5 g of cobalt chloride hexahydrate and 37.5 ml of 2-butanone. After replacing the atmosphere of the system by nitrogen, the mixture was heated in a water bath and a solution of sodium borohydride (20 g)/2N sodium hydroxide (1 ml)/water (100 ml) was added dropwise thereto under stirring at an inner temperature of 35° C. After stirring for 2 hours as it was, the mixture was cooled to 15° C. and then stirred overnight. Thereto was added 37.5 ml of 2-butanone, followed by stirring for 1 hour. Then, the precipitates were collected by filtration and dried, to give a crude product of the title compound. Thereto was added 700 ml of a 50% methanol aqueous solution, and the mixture was heated at 40° C., filtered and washed with 300 ml of a 50% acetone aqueous solution. After the mixture was adjusted to pH 6.5 with concentrated hydrochloric acid, methanol was evaporated. To the residue was added dropwise 2250 ml of acetone, followed by stirring at 20° C. overnight. Precipitated crystals were collected by filtration and dried, to give 45.0 g of the title compound (yield 90.7%).

Example 7

Synthesis of Mecobalamin

The present example was conducted in the dark place (under infrared ray).

To 130 ml of ion-exchanged water were added 10 g of cyanocobalamin, 3.48 g of trimethylsulfonium bromide, 700 mg of cobalt chloride hexahydrate, and 7.5 ml of 2-butanone. After replacing the atmosphere of the system by nitrogen, the whole was warmed on a water bath and a solution of sodium borohydride (4 g)/2N sodium hydroxide (0.2 ml)/water (20 ml) was added dropwise thereto under stirring at an inner temperature of 35° C. After stirring for 3 hours as it was, the mixture was cooled to 15° C. and then stirred overnight. Thereto was added 7.5 ml of butanone, followed by stirring for 2 hours. Then, the precipitates were collected by filtration and dried, to give a crude product of the title compound. Thereto was added 140 ml of a 50% acetone aqueous solution and the mixture was heated at 45° C., filtered and washed with 60 ml of a 50% acetone aqueous solution. After the mixture was adjusted to pH 6.5 with concentrated hydrochloric acid, 475 ml of acetone was added dropwise thereto and the mixture was stirred at 20° C. overnight. Precipitated crystals were collected by filtration and dried, to give 8.94 g of the title compound (yield 90.1%).

Example 8

Synthesis of Mecobalamin

The present Example was conducted in the dark place (under infrared ray).

To 130 ml of ion-exchanged water were added 10 g of cyanocobalamin, 2.85 g of trimethylsulfoxonium chloride, 700 mg of iron (II) sulfate heptahydrate and 7.5 ml of 2-butanone. After replacing the atmosphere of the system by nitrogen, the mixture was heated in a water bath. A solution of sodium borohydride (4 g)/2N sodium hydroxide (0.5 ml)/water (20 ml) was added dropwise thereto under stirring at an inner temperature of 35° C. After stirring for 3 hours as it was, the mixture was cooled to 15° C. and then stirred overnight. Thereto was added 7.5 ml of butanone, followed by stirring for 2 hours. Then, the precipitates were collected by filtration and dried, to give 35 g of a crude product of the title compound. Thereto was added 140 ml of a 50% acetone aqueous solution. The mixture was heated at 45° C., filtered and washed with 60 ml of a 50% acetone aqueous solution. After the mixture was adjusted to pH 6.5 with concentrated hydrochloric acid, 475 ml of acetone was added dropwise thereto and the mixture was stirred at 20° C. overnight. Precipitated crystals were collected by filtration and dried, to give 8.92 g of the title compound (yield 89.9%).

What is claimed is:

1. A process for producing methylcobalamin (V), which comprises the step of methylating cyanocobalamin (I) or hydroxocobalamin (II) represented by the following formula:

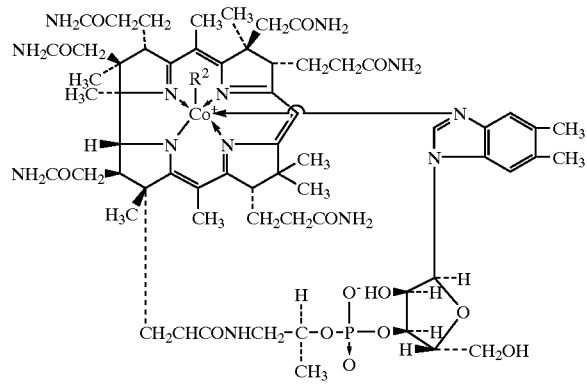

$R^2$=CN: Cyanocobalamin (I)
$R^2$=OH: Hydroxocobalamin (II)
$R^2$=CH$_3$: Methylcobalamin (V)

in the presence of a reducing agent (III) and a water-soluble methylating agent (IV) wherein the water-soluble methylating agent is represented by the formula (VI)

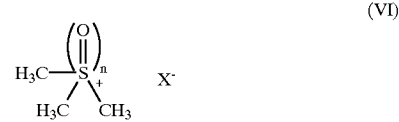

(VI)

and wherein X means a halogen atom or methoxysulfonyloxy group;

and n means 0 or 1.

2. A process for producing methylcobalamin (V), which comprises the step of methylating cyanocobalamin (I) or hydroxocobalamin (II) in the presence of a reducing agent (III) and a water-soluble methylating agent (IV) in an aqueous solution or a hydrous organic solvent;

wherein the water-soluble methylating agent is represented by the formula (VI)

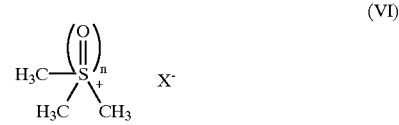

(VI)

and wherein X means a halogen atom or methoxysulfonyloxy group;

and n means 0 or 1.

3. A process for producing methylcobalamin (V), which comprises the steps of methylating cyanocobalamin (I) or hydroxocobalamin (II) in the presence of a reducing agent (III) and a water-soluble methylating agent (IV) in an aqueous solution or a hydrous organic solvent;

wherein the water-soluble methylating agent is represented by the formula (VI)

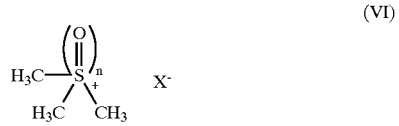

(VI)

and wherein X means a halogen atom or methyoxysulfonyloxy group;

and then precipitating the reaction product as crystals or precipitates.

4. A process for producing methylcobalamin (V), which comprises the steps of methylating cyanocobalamin (I) or hydroxocobalamin (II) in the presence of a cyan ion-trapping agent, a reducing agent (III) and a water-soluble methylating agent (IV) in an aqueous solution or a hydrous organic solvent wherein the water-soluble methylating agent is represented by the formula (VI)

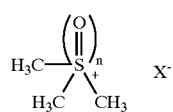

(VI)

and wherein X means a halogen atom or methoxysulfonyloxy group;

and n means 0 or 1;

and then precipitating the reaction product as crystals or precipitates.

5. The process for producing methylcobalamin (V) according to any one of claims 1 to 4, wherein the trimethylsulfur derivative (VI) is at least one selected from trimethylsulfoxonium iodide, trimethylsulfonium iodide, trimethylsulfoxonium bromide, trimethylsulfonium bromide, trimethylsulfoxonium chloride and trimethylsulfonium chloride.

6. The process for producing methylcobalamin (V) according to any of claims 1 to 4, wherein the reducing agent (III) is sodium borohydride.

7. The process for producing methylcobalamin (V) according to claim 4, wherein the cyan ion-trapping agent is at least one selected from ferrous sulfate and cobalt chloride.

8. The process for producing methylcobalamin (V) according to claim 4 or 7, wherein the amount of the cyan ion-trapping agent is from 1 to 30% by weight relative to cyanocobalamin (I) or hydroxocobalamin (II).

9. The process for producing methylcobalamin (V) according to any of claims 1 to 4, wherein the trimethylsulfur derivative (VI) is at least one selected from trimethylsulfoxonium iodide, trimethylsulfonium iodide, trimethylsulfoxonium bromide, trimethylsulfonium bromide, trimethylsulfoxonium chloride and trimethylsulfonium chloride; and the reducing agent (III) is sodium borohydride.

10. The process for producing methylcobalamin (V) according to claim 4, wherein the trimethylsulfur derivative (VI) is at least one selected from trimethylsulfoxonium iodide, trimethylsulfonium iodide, trimethylsulfoxonium bromide, trimethylsulfonium bromide, trimethylsulfoxonium chloride and trimethylsulfonium chloride; the reducing agent (III) is sodium borohydride; and the cyan ion-trapping agent is at least one selected from ferrous sulfate and cobalt chloride.

* * * * *